United States Patent [19]

Vicari et al.

[11] Patent Number: 5,464,941
[45] Date of Patent: Nov. 7, 1995

[54] BIPHENYL PYRAZINE COMPOUNDS

[75] Inventors: Richard Vicari; George Kvakovszky; Olan S. Fruchey, all of Corpus Christi, Tex.; Hans J. Metz, Darmstadt, Germany

[73] Assignee: Hoechst Celanese Corporation, Somerville, N.J.

[21] Appl. No.: 326,103

[22] Filed: Oct. 19, 1994

[51] Int. Cl.$^6$ ........................ C07C 245/08; C09B 35/03; C07D 241/00
[52] U.S. Cl. .......... 534/741; 534/797; 534/560; 544/359; 544/384; 544/403; 544/357; 544/398; 544/401; 528/68; 524/190
[58] Field of Search ................... 534/741, 797; 544/359, 384, 357, 398, 401, 403

[56] References Cited

U.S. PATENT DOCUMENTS

| | | | |
|---|---|---|---|
| 2,838,486 | 6/1958 | Mueller et al. | 534/741 |
| 3,157,667 | 11/1964 | Kern et al. | 534/741 X |
| 4,051,123 | 9/1987 | Piller et al. | 534/792 X |
| 4,568,623 | 2/1986 | Makino et al. | 430/58 |
| 4,847,364 | 7/1989 | Mockli | 534/605 |

FOREIGN PATENT DOCUMENTS

| | | | |
|---|---|---|---|
| 59-45444 | 3/1984 | Japan | 534/741 |
| 63-91377 | 4/1988 | Japan | 544/384 |

*Primary Examiner*—Floyd D. Higel
*Attorney, Agent, or Firm*—James J. Mullen; Donald R. Cassady

[57] ABSTRACT

The present invention provides novel substituted biphenyl pyrazines or pyrazine derivatives ("BPD") which are functional and have useful application as a monomer for a variety of high performance polymers such as polyester, polyarylate, polycarbonate, polyetherketones, epoxies, polyimides, polyamides, and polyamides-imides; and as pigments for coating compositions such as paints. These BPD have the formula:

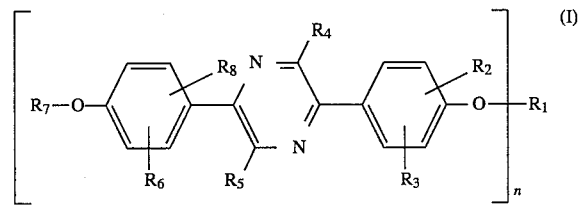

14 Claims, No Drawings

BIPHENYL PYRAZINE COMPOUNDS

BACKGROUND OF THE INVENTION

Field of the Invention

The present invention relates to novel derivatives of pyrazine (substituted biphenyl pyrazines), to processes for preparing them, to compositions which contain the novel compounds, and to the use of said compositions for a wide variety of end use applications.

Related Applications

The present patent application is commonly owned by the same Assignee as the following cases:

(a) Ser. No. 08/326,104 filed Oct. 19, 1994, entitled "Polymer Compositions Containing Substituted Biphenyl Pyrazines".

Description of Related Art

The following prior art references are disclosed in accordance with the terms 37 CFR 1.56, 1.97, and 1.98.

Japanese patent publication no. 02-138267 (issued May 28, 1990) discloses the preparation of pyrazine derivatives for liquid crystals.

Japanese patent publication no. 02-072370 (issued Mar. 12, 1990) discloses electrophotographic photoreceptors containing pyrazine derivatives.

U.S. Pat. No. 3,761,477 discloses pyrazine-acetic acids, acetates, and acetamides which may be used as ultraviolet absorbers in plastics and resins.

U.S. Pat. No. 3,963,715 (issued Jun. 15, 1976) discloses various substituted pyrazines useful as dyes and pigments.

U.S. Pat. No. 5,099,344 (issued Mar. 24, 1992) discloses various substituted pyrazines useful in a ferroelectric liquid crystal device.

*Bull. Soc. Chem. Fr.*, (12), 4970-4 (N. Vinot/J. Pinson) discloses various pyrazine derivatives.

*Bull. Soc. Chem. Fr.*, p. 533 (1949) (G. Muller et al.) discloses the preparation of various pyrazine derivatives.

J. Chem. Soc. 97, p. 2495 (1910) discloses the preparation of various pyrazine derivatives.

Chemical Abstracts, Vol. 108, 1988, (151196t) discloses the use of various pyrazines for polyimides.

Chemical Abstracts, Vol. 108, 1988, (223028q) discloses the manufacture of polyester-polycarbonates using various pyrazines.

Chemical Abstracts, Vol. 114, 1988, (165442f) discloses polyaramids having incorporated therein various pyrazines.

Chemical Abstracts, Vol. 115, 1991, (49064f) discloses the preparation of various pyrazines useful as monomers and hardening agents for epoxy resins and urethane polymers.

Ueta et al., Polymer Journal, Vol. 24, No. 12, pp. 1429–1436 (1992) discloses the synthesis and properties of novel p-aramid including pyrazine ring.

All of the above-cited prior art patents and articles (and any others cited herein) are incorporated herein by reference in their entirety.

SUMMARY OF THE INVENTION

The present invention provides novel substituted biphenyl pyrazines or biphenyl pyrazine derivatives ("BPD") which are functional and have useful application as a monomer (co-monomer) for a variety of high performance polymers such as polyester, polyarylate, polycarbonate, polyetherketones, epoxides, polyimides, polyamides, and polyamides-imides; and as dyes and pigments for coating compositions such as paints. These BPD have the general formula:

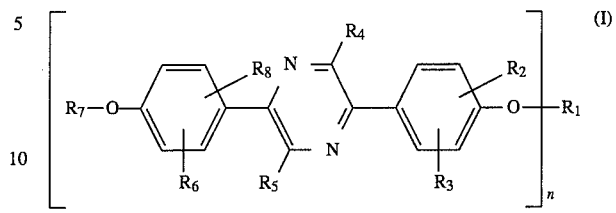

wherein $R_{1-8}$ and n are defined below.

DETAILED DESCRIPTION OF THE INVENTION

The present invention provides novel biphenyl pyrazine derivatives ("BPD") which are derivatives of substituted and unsubstituted acetophenone, e.g. 4-hydroxyacetophenone (4-HAP), which is a well-known basic building block for numerous organic chemicals. BPD, in turn, are building blocks for high performance polymers, heretofore mentioned, and pigment compositions. These BPD have the general formula:

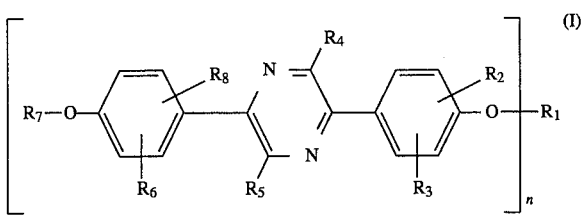

wherein n is 1 or 3, with the proviso that:

A) where n is 1,
   (i) $R_1$ and $R_7$ are each independently selected from the group consisting of H and —$CH_2C_6H_5$,
   (ii) $R_2$, $R_3$, $R_6$, and $R_8$ are each independently selected from the group consisting of H, halogen, $NO_2$, $NH_2$, $N_2\oplus$, $SO_3H$, $SO_3M$ (where m is an alkali metal such as sodium, potassium), $C_6H_5$, —$OR^1$ (R'=$C_{1-8}$),

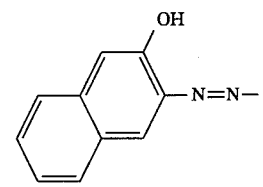

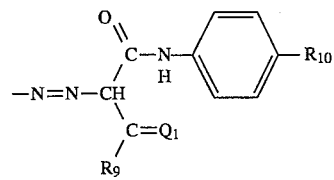

where $R_9$ and $R_{10}$ are each H, $C_1$–$C_6$, $COOCH_3$, and $COOC_2H_5$, and $Q_1$ is NH or O;

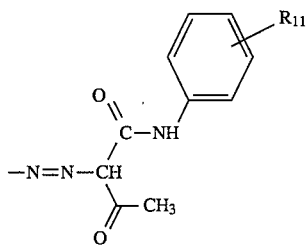

where $R_{11}$ is $C_1$–$C_6$;

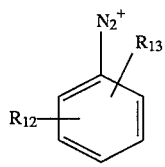

where $R_{12}$ and $R_{13}$ are each independently selected from the group consisting of H, $NO_2$, CN, halogen (eg. Cl), $OCH_3$, COOH, $COOCH_3$, $NH_2$,

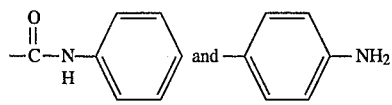

with the proviso that at least one of $R_2$, $R_3$, $R_6$, and $R_8$ must be other than H;

B) where n is 3,

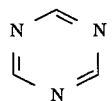

and $R_2$, $R_3$, $R_6$, $R_7$, and $R_8$ are the same as in (A) above;

C) where n is 1 or 3, $R_4$ and $R_5$ are each independently selected from the group consisting of H, $NO_2$, $NH_2$, and

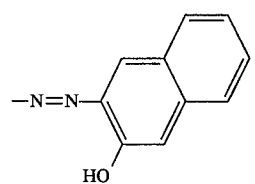

Various BPD are set forth below to illustrate the compounds falling within Formula I above:

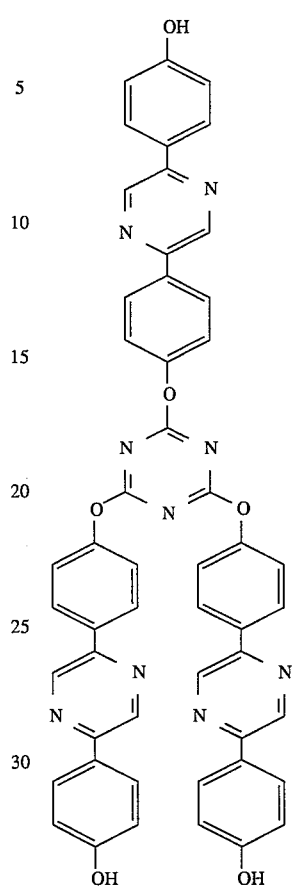

(II)

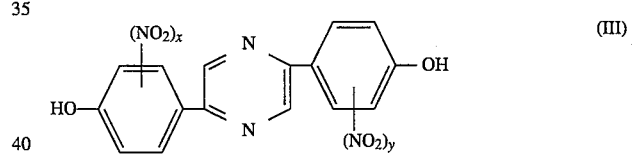

(III)

where x and y are each independent and are either 0, 1, or 2, with the proviso that at least x or y must be 1 or 2 when the other is 0.

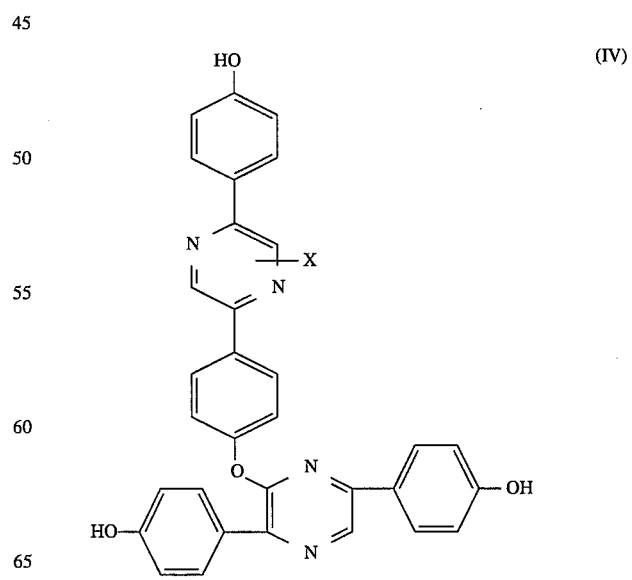

(IV)

where x is halogen such as chlorine, fluorine, or bromine;

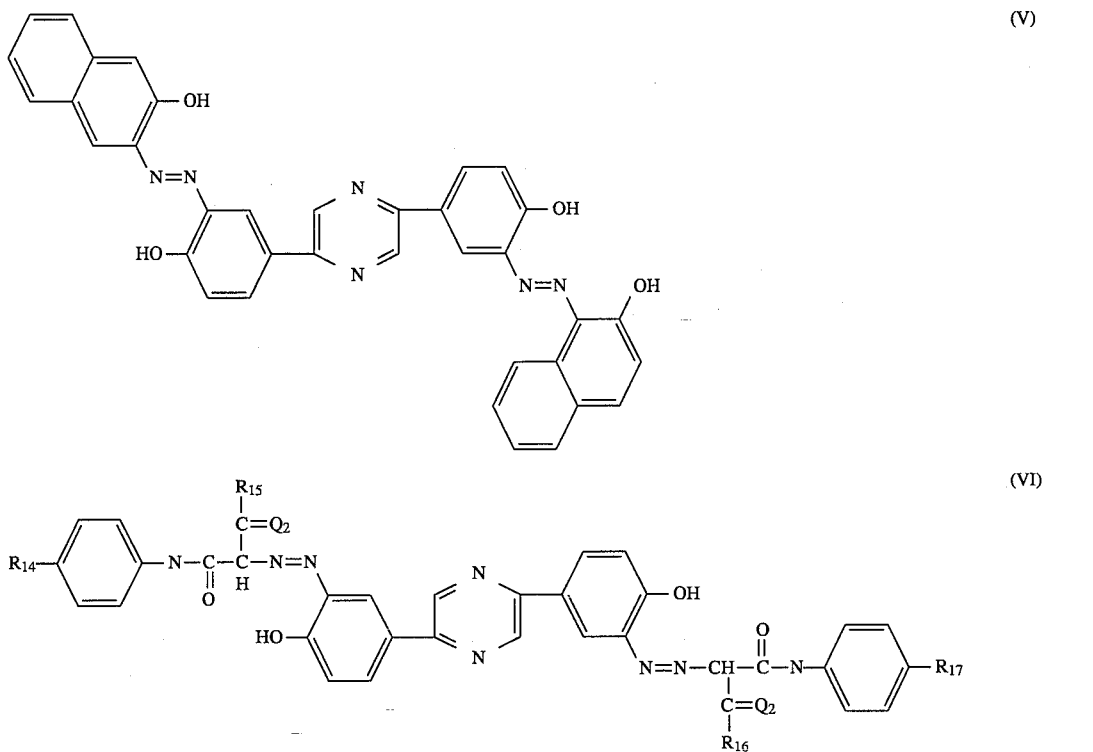

(V)

(VI)

wherein $R_{14}$, $R_{15}$, $R_{16}$, and $R_{17}$ are each independently selected from the group consisting of H, alkyl $C_1$–$C_6$, $COOCH_3$, and $COOC_2H_5$, and $Q_2$ is NH or O.

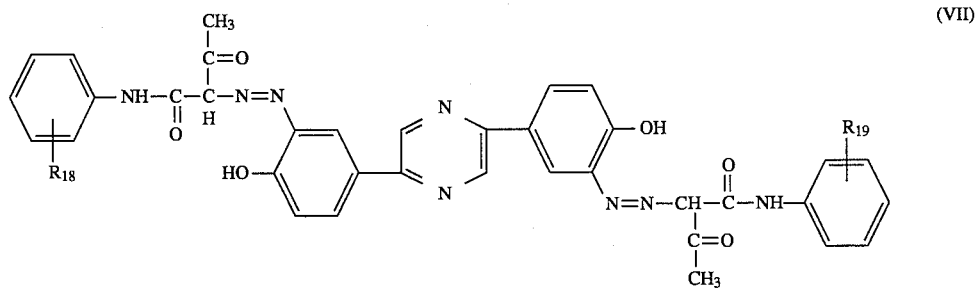

(VII)

wherein $R_{18}$ and $R_{19}$ are each independently selected from the group consisting of H, alkyl $C_1$–$C_6$, $COOCH_3$ and $COOC_2H_5$.

In general, the substituted biphenyl pyrazines are prepared by self condensing a substituted alpha keto amine to form a substituted dihydropyrazine and then oxidizing the substituted dihydropyrazine to form the corresponding substituted biphenyl pyrazine. The substituted alpha keto amines, also called arylketoamines such as aminohydroxyacetophenone ("AHAP"), can be prepared by the methods described in copending U.S. patent application Ser. No. 08/191,849, now U.S. Pat. No. 5,349,090, entitled "Process for Preparing Arylketoamines" filed Feb. 4, 1994. The substituted alpha keto amines may also be prepared by those processes set forth in U.S. Pat. Nos. 1,995,709; 2,567,906; 2,505,645; 2,784,228; 3,028,429; 3,966,813; 5,124,489; and 5,198,585. All of these references are incorporated herein by reference in their entirety.

Where one so desires to start the preparation of the substituted biphenyl pyrazines or novel biphenyl pyrazine derivatives (all BPD) from a commercially available material such as a substituted or unsubstituted acetophenone (such as 4-hydroxyacetophenone, "4-HAP"), such acetophenone can be subjected to nitrite oxidation conditions to form the substituted or unsubstituted phenylglyoxal which, in turn, is oximated with a substituted amine to form the substituted or unsubstituted alpha-keto-oxime. This oxime is catalytically hydrogenated to form the corresponding substituted or unsubstituted alpha-keto-amine. The overall five-step method is set forth below in Scheme 1. Examples of materials used to facilitate the basic reaction are shown. In Scheme 1, Ar is representative of substituted phenyl groups in Formula I above.

SCHEME 1

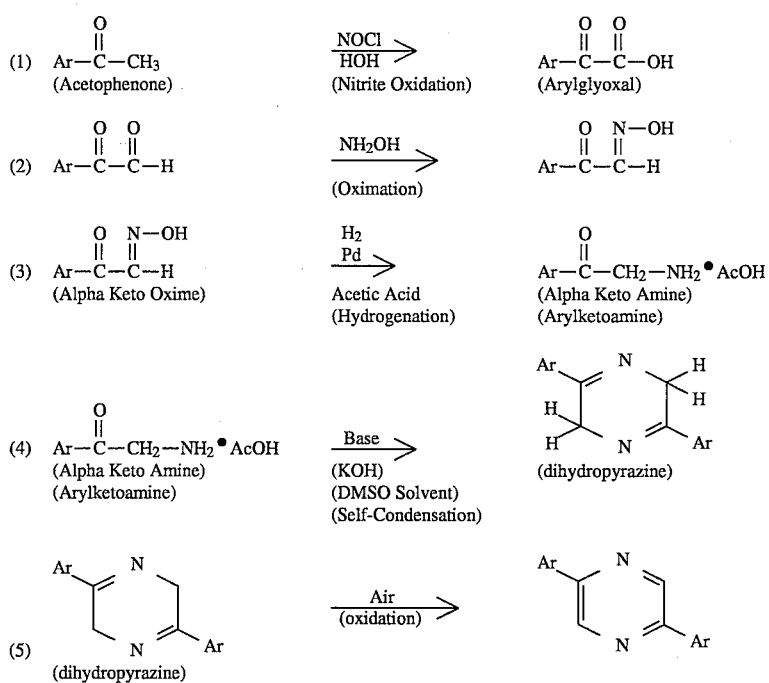

In step (1), Scheme 1 above, an acetophenone, substituted or unsubstituted, is subjected to nitrite oxidation conditions to form the substituted or unsubstituted phenylglyoxal. The nitrite oxidation conditions consist of reacting such acetophenone (e.g. 4-HAP) in an aqueous medium with nitrosyl chloride (NOCl) to form the corresponding phenylglyoxal.

In step (2), Scheme 1 above, the phenylglyoxal is oximated with a substituted amine, such as $NH_2OH$, to form the substituted or unsubstituted alpha keto oxime, such as 4-hydroxy-α-isonitrosoacetophenone ("HINAP").

In step (3), Scheme 1 above, the substituted or unsubstituted alpha keto oxime (e.g. HINAP) is subjected to catalytical hydrogenation to form the corresponding substituted or unsubstituted alpha keto amine. Such hydrogenation is effected by the use of hydrogen in the presence of a transition metal catalyst and a liquid carboxylic acid at a temperature of less than about 50° C., preferably from about 10° C. to about 35° C. Generally this reaction is conducted in the absence of a dipolar aprotic solvent. The liquid carboxylic acid is selected from the group consisting of formic, acetic, propanoic, butyric, valeric, caproic, heptanoic, octanoic, nonanoic, undecanoic, isobutyric, isovaleric, cyclohexane carboxylic acid, and mixtures thereof. The liquid carboxylic acid is further characterized by one which is capable of substantially dissolving the alpha keto oxime therein. The transition metal (catalyst) is selected from the group consisting of platinum, palladium, nickel, rhodium, and combinations thereof. This transition metal catalyst is preferably on an inert support such as carbon and/or barium sulfate. Where the aryl group is halogenated, it is desirable to use a Lindlar catalyst (e.g. palladium on barium sulfate) to insure halogen stability.

In step (4), Scheme 1 above, the substituted or unsubstituted alpha keto amine such as amino-hydroxyacetophenone (AHAP), are subject to self-condensing conditions to form the corresponding substituted or unsubstituted dihydropyrazine. These condensation conditions include the use of a dipolar aprotic solvent and a base material such as sodium or potassium hydroxide. Such dipolar aprotic solvents employed are solvents which have a high dielectric constant and a high dipole moment but no acid hydrogen atoms. Such solvents include, without limitation, dimethylsulfoxide (DMSO), acetonitrile, n-methyl-pyrrolidone (NMP), dimethylformamide (DMF), dimethylacetamide, and hexamethylphosphoric acid triamide (HMPT).

In step (5), Scheme 1 above, the substituted or unsubstituted dihydropyrazine is subjected to oxidation conditions to produce the substituted or unsubstituted pyrazines of the present invention. This oxidation reaction can employ any means to facilitate an oxidation of the dihydropyrazine to form the desired end product, i.e. BPD. This oxidation is generally conducted at a temperature less than those temperatures employed in step (4) above regarding the self-condensing action.

In conjunction with step 5 (Scheme I), the resultant product (starting from 4-HAP) will be 2,5-bis(4-hydroxyphenyl)pyrazine (sometimes referred to herein as "pyrazine") which has the following structure:

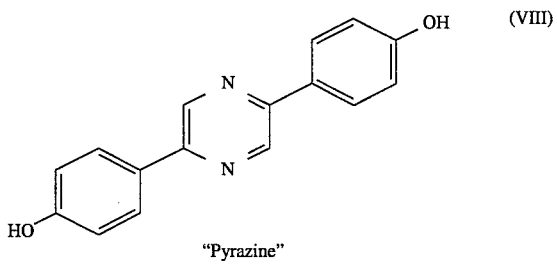

"Pyrazine" (VIII)

Since this can be easily made, it is preferred that this material be used as the starting material for the preparation of the novel substituted biphenyl pyrazines (BPD) of the present invention. The following schemes will illustrate the preparation of the various BPD following within Formula I above.

With reference to Scheme 2, the basic starting material, i.e. "pyrazine" (Formula VIII) can be subjected to nitration to form the dinitro "pyrazine" (Formula IX). The general reaction conditions are conducted at temperatures less than about 100° C., and preferably from about 0° C. to about 50° C. The reaction pressures can be subatmospheric, atmospheric, or super atmospheric. Where one so desires, suitable solvents can be employed to facilitate the reaction and used in place of water or as a co-solvent with water. The mononitro "pyrazine" (Formula X) can be prepared by the partial hydrolysis of the ester of pyrazine followed by partial nitration and partial hydrolysis as shown in the bottom portion of Scheme 2. The tetranitro "pyrazine" (Formula III, x=2 and y=2) can be prepared via nitration under more aggressive conditions, such as with mixtures of nitric and sulfuric acids.

variety of BPD as shown in Scheme 3.

| 1) Reduction of nitro compounds | preparation of amines |
| 2) Diazotization | preparation of diazonium salts |
| 3) Diazo coupling | preparation of pigments |

SCHEME 2

Nitration

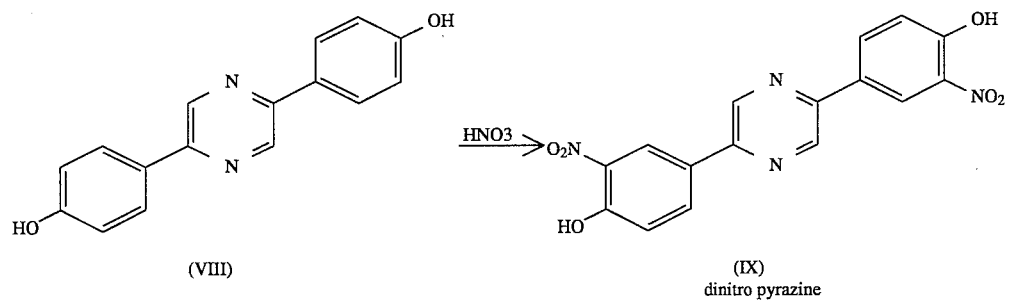

Indirect mono-nitration

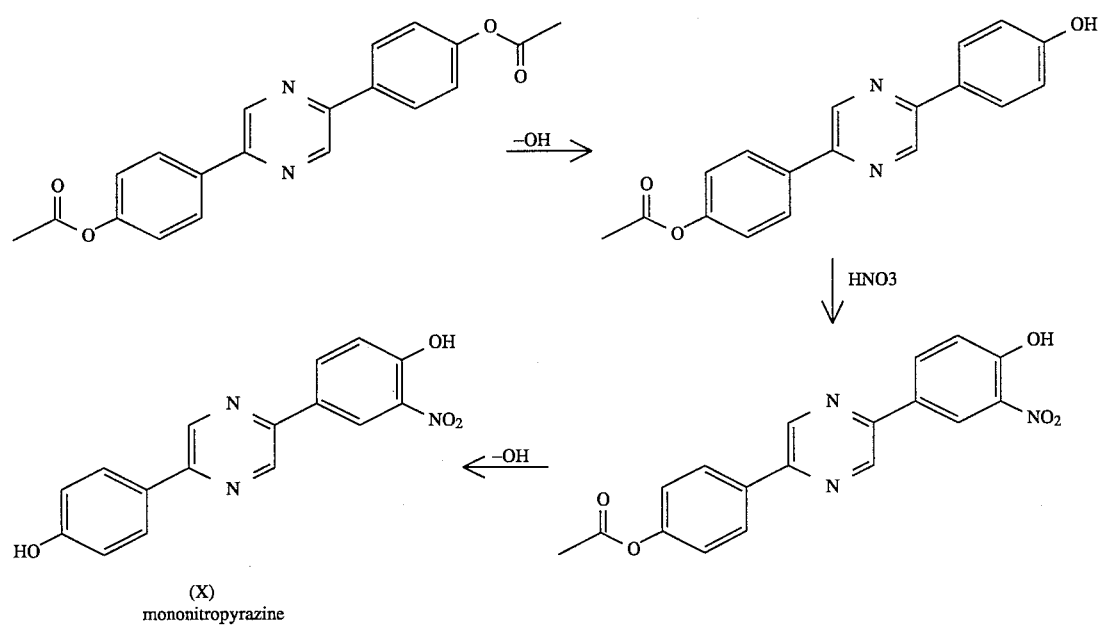

Once the nitro compounds of Scheme 2 are prepared, these may be subjected to the following steps to form a wide

SCHEME 3
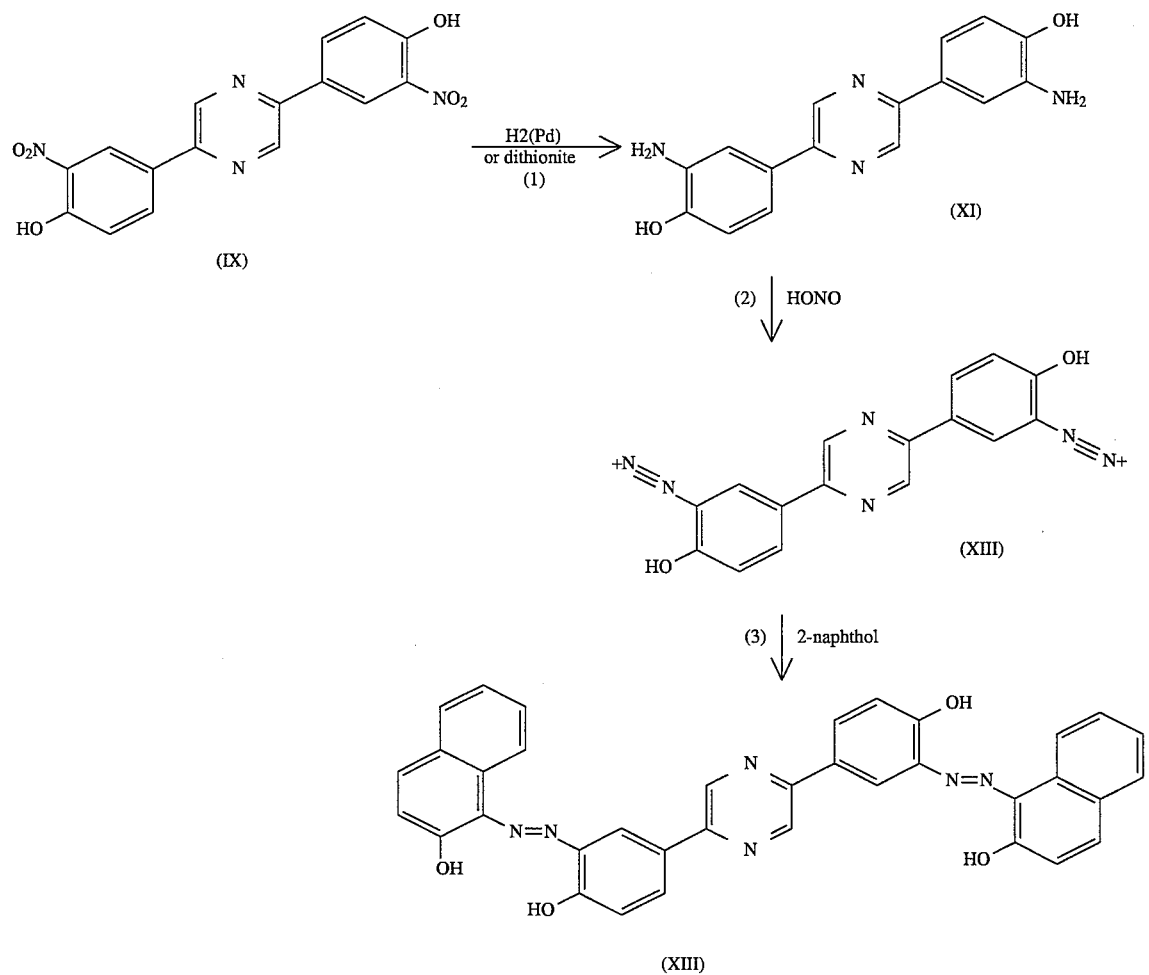
The diazonium salts (Formula XII) can undergo additional coupling reactions as shown in Scheme 4 below.
SCHEME 4
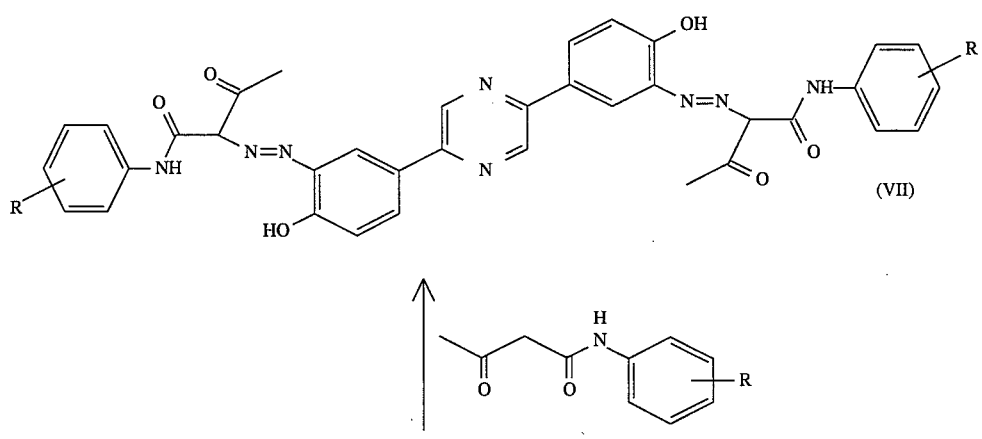

-continued
SCHEME 4

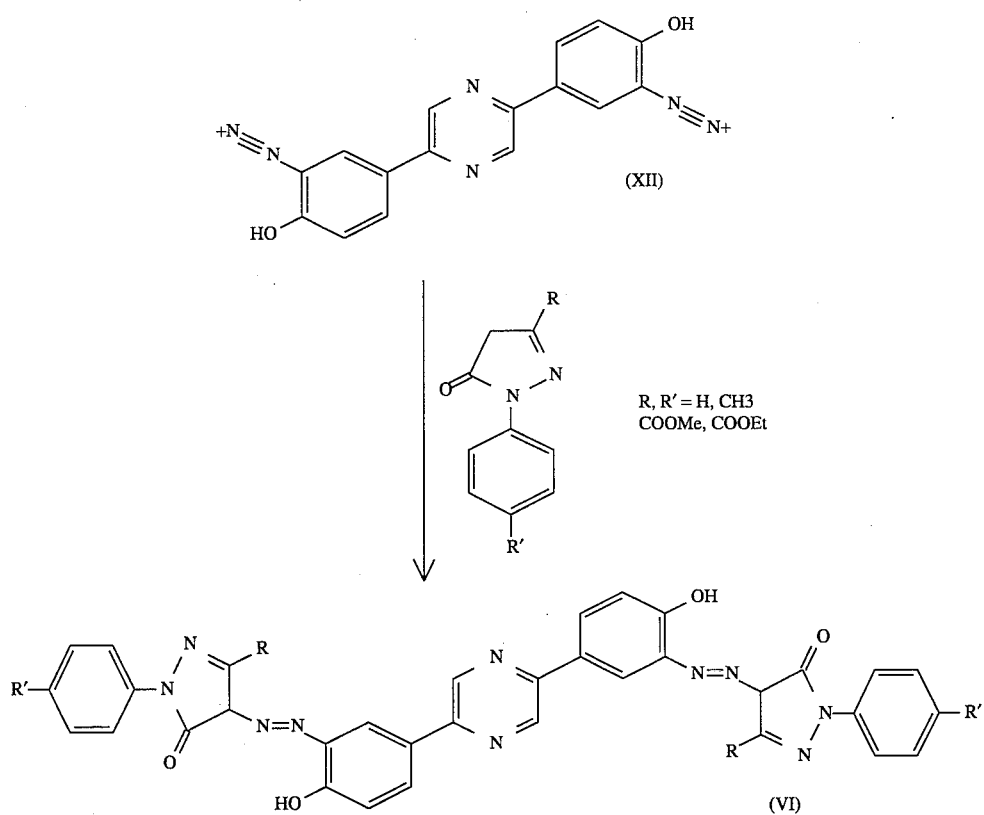

As can be seen in Schemes 3 and 4 above, these process steps permit the preparation of BPD which fall within Formulae VI and VII set forth above.

Referring to Formula XII, the diazonium salts may be used in a similar manner to provide additional substrates for diazo coupling to the pyrazine. These substrates and the location of coupling are shown in Scheme 5 below (the arrow is the place of coupling).

SCHEME 5

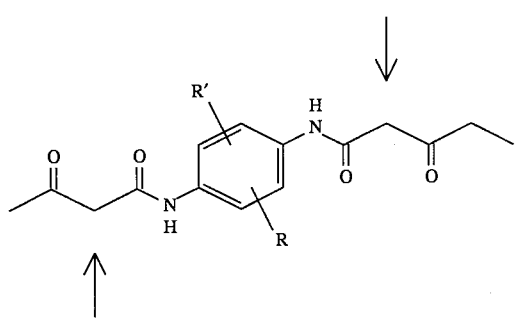

-continued
SCHEME 5
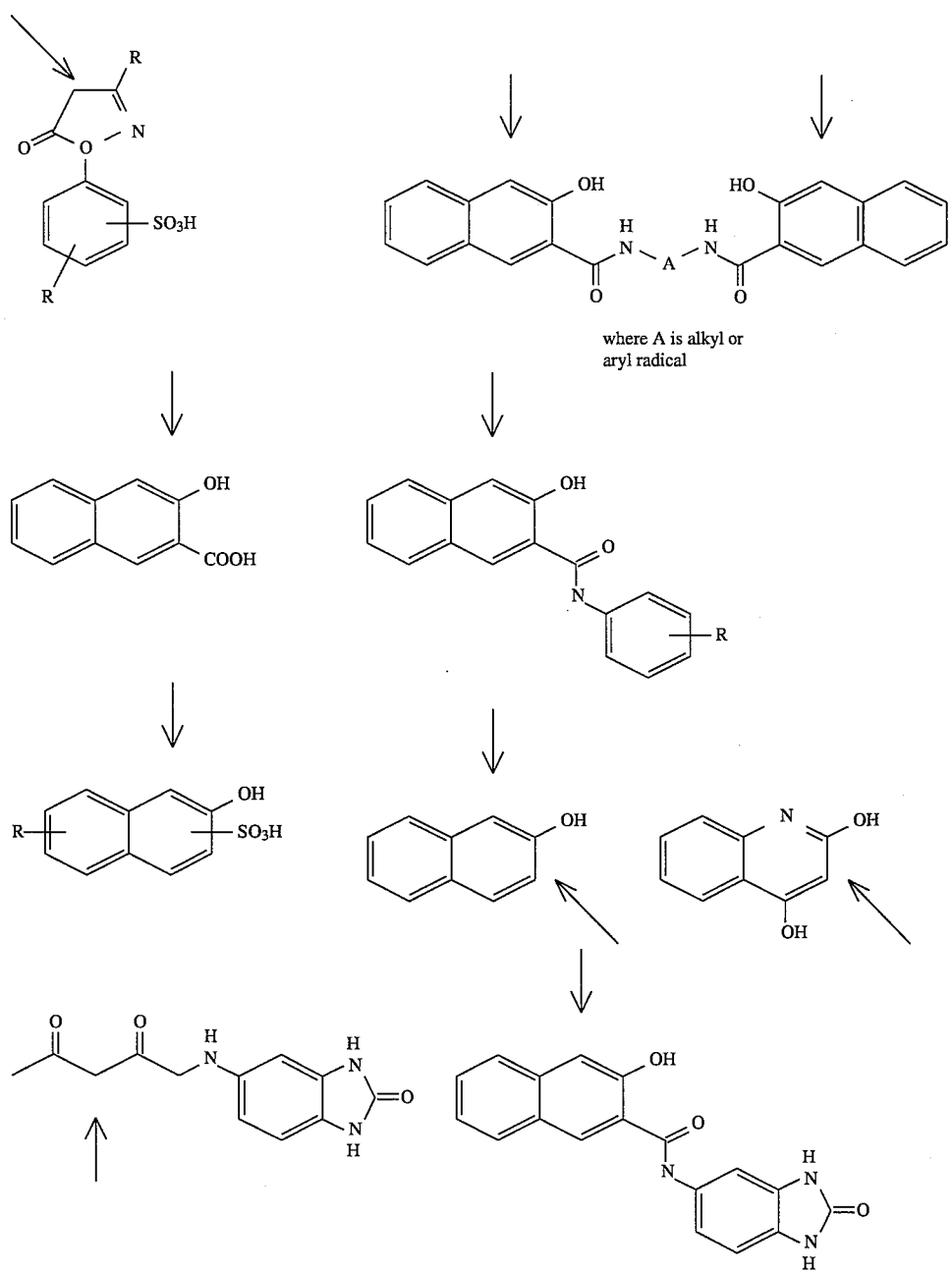
where A is alkyl or aryl radical
The following process (Scheme 6) discloses the preparation of ring substituted amines and diazonium salts.

SCHEME 6

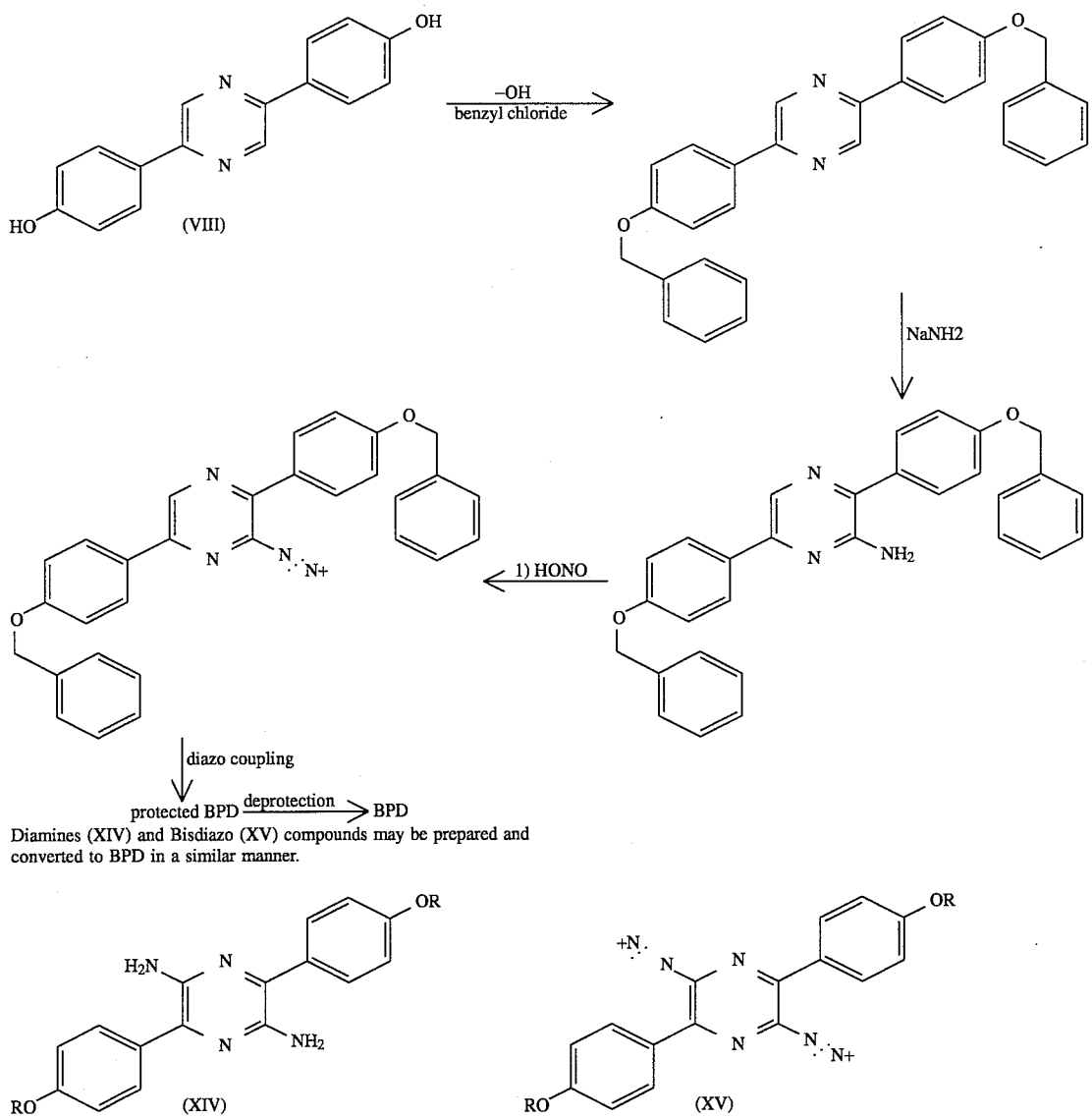

Diamines (XIV) and Bisdiazo (XV) compounds may be prepared and converted to BPD in a similar manner.

Scheme 7 shows the preparation of BPD wherein the pyrazine ring contains a halogen atom such as chlorine. In oxidizing the pyrazine ring, this is conducted with a peracid or perester, with or without a solvent. The most preferred oxidizing agent is hydrogen peroxide. Others, non-exclusively, include peracetic acid, alkyl peroxides, chloroperacetic acid, peroxybenzoic acid, and meta-chloroperoxybenzoic acid and trifluoro-peroxyacetic acid. Various solvents can be used in the overall reaction and these include, non-exclusively, water, alcohol, or polar aprotic solvents (e.g. ketones, ethers, nitriles, and sulfides), halogenated hydrocarbons, and carboxylic acids such as acetic acid. The reaction may take place at from about 0.01 to about 24 hours, or more preferably, from about 0.1 to about ten hours at a temperature of from about 0° C. to about 100° C., or more preferably, from about 25° C. to about 75°. The reaction may take place at either elevated or reduced pressures, in addition to atmospheric pressure. Where heat is generated during the reaction, it may be desirable to conduct the reaction at a reduced pressure in order to remove heat by evaporation of the solvent.

In Scheme 7, the chlorination can be conducted using any means to supply chlorine as long as such means do not prevent the basic reaction from taking place and/or promote the formation of undesirable by-products or the incorrect product. Scheme 7 shows the use of $POCl_3$, but other chlorinating agents can be used. Likewise, other halogens can be similarly attached directly to the pyrazine ring. The reaction conditions are generally disclosed immediately above in describing the oxidation step.

In the third step in Scheme 7, the halogenated pyrazine ring compound (XVI) can then be subjected to a self-condensation step, under basic conditions, in order to add a second "pyrazine" substituent. This self-condensation step can be carried out in the same manner as described in step 4 of Scheme 1 above.

SCHEME 7

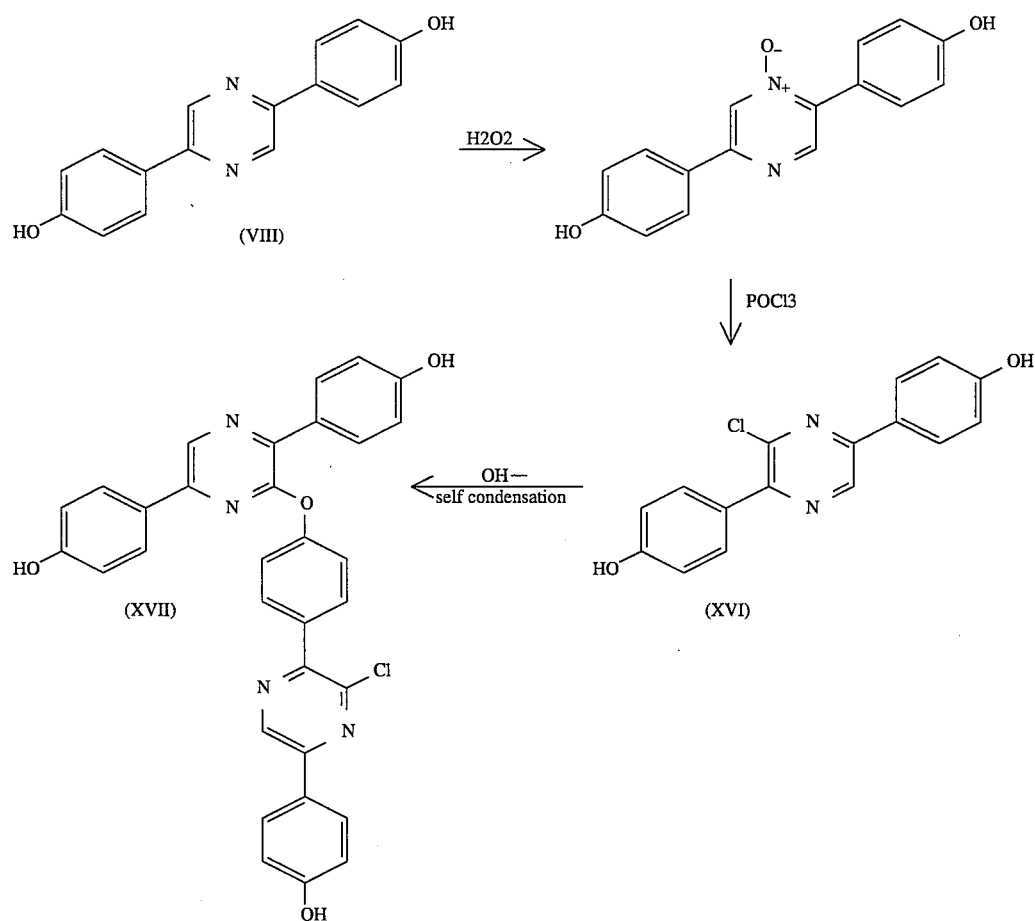

Scheme 8 discloses the preparation of BPD wherein n=3. In general, the process comprises reacting a trihalocyanurate, such as trichlorocyanurate, with the basic "pyrazine" (Formula VIII) in a base material, such as sodium hydroxide, with or without a suitable solvent (the temperatures and pressures are not critical). The temperature is generally in the range of from about 0° C. to about 150° C.

SCHEME 8

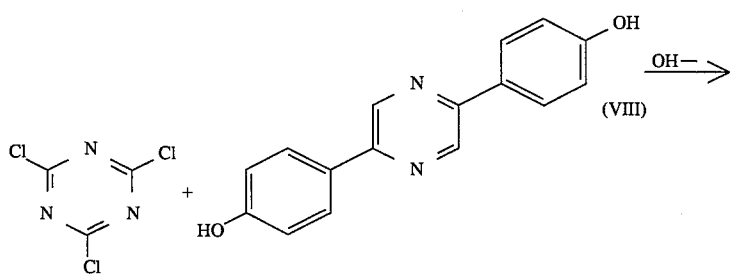

-continued

SCHEME 8

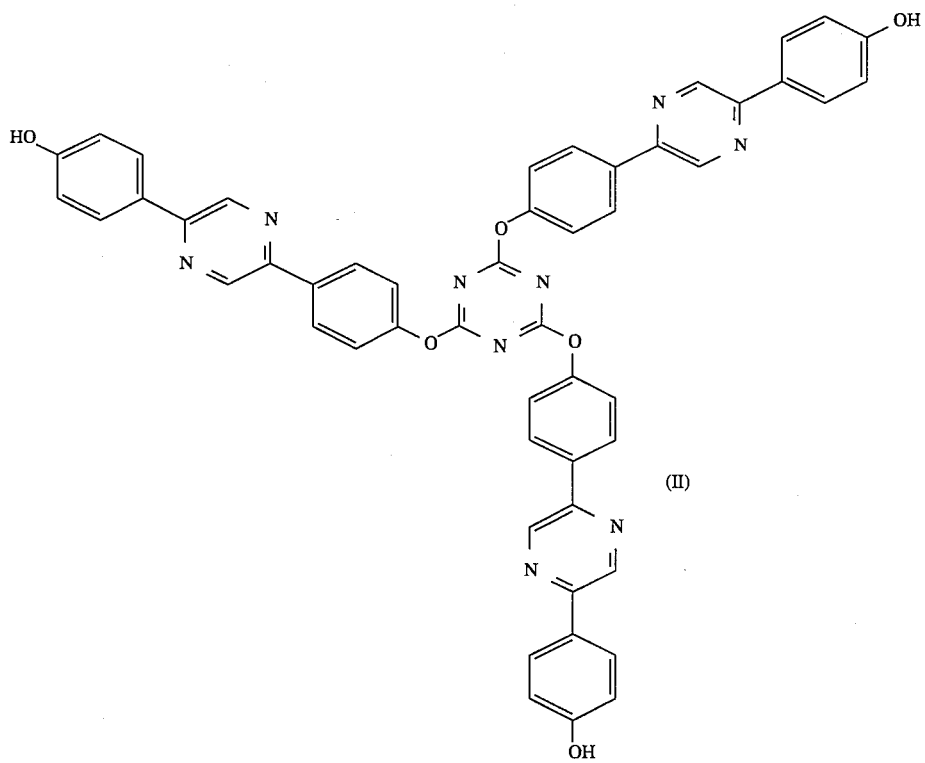

(II)

Scheme 9 discloses the preparation of BPD by the diazo coupling of pyrazine with anilines. The scheme 9 chart also discloses other anilines that can be used for the diazo coupling. Examples of anilines and substituted anilines are as follows:

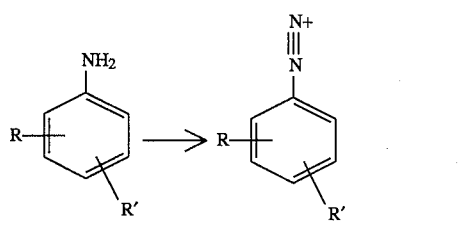

where R and R' are each independently selected from the group consisting of H, $NO_2$, Cl, $CH_3$, $OCH_3$, COOH, $COOCH_3$, $NH_2$, $C(O)N(H)C_6H_5$, and —$C_6H_4NH_2$.

SCHEME 9

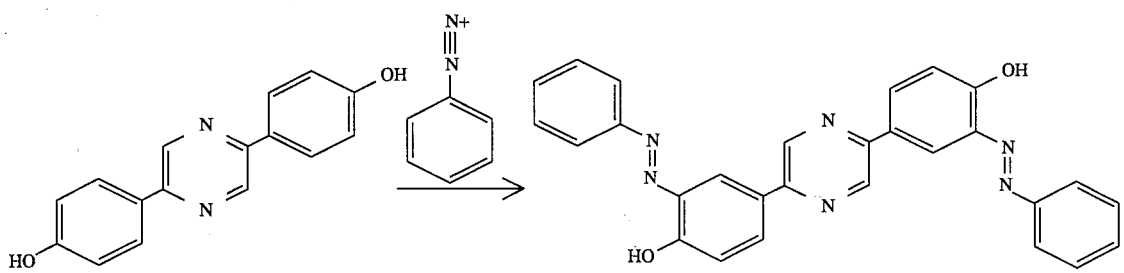

-continued
SCHEME 9

OTHER ANILINES FOR DIAZO COUPLING TO PYRAZINE:

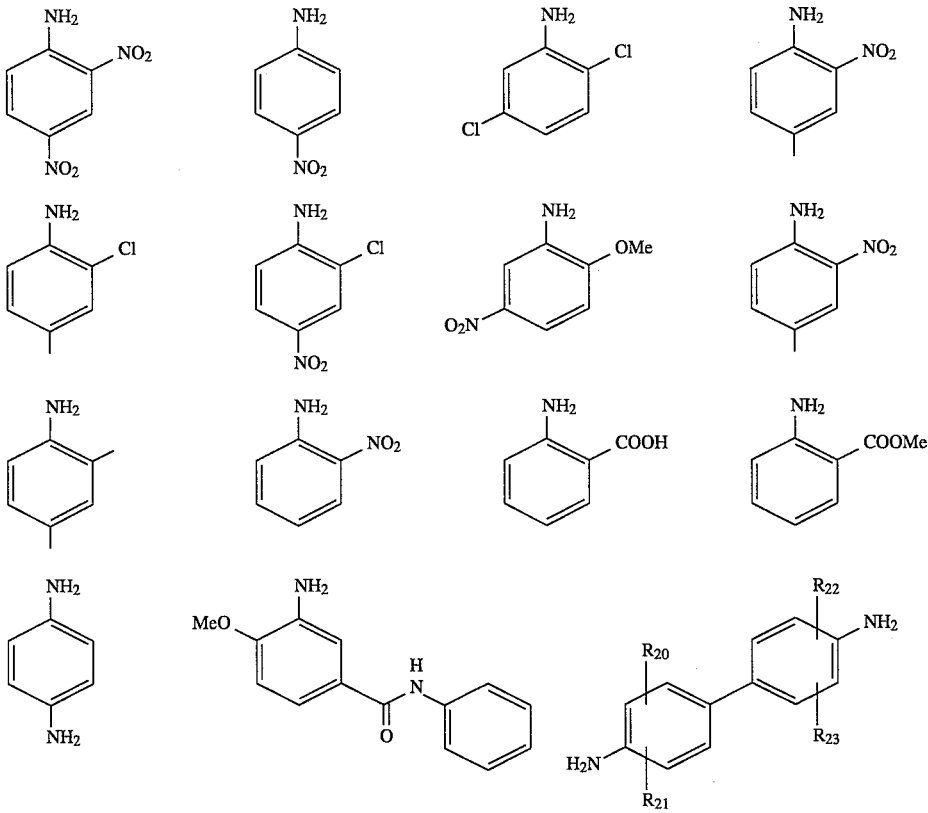

where $R_{20}$, $R_{21}$, $R_{22}$, and $R_{23}$ are each independently selected from the group consisting of H, Cl, $CH_3$, and $OCH_3$.

The diazo coupling outlined herein and with reference to Scheme 9 can be carried out by those processes well-known in the an and also as outlined in *Organic Chemistry*, 3rd Edition, Morrison & Boyd, 1973, Allyn & Bacon, Inc. (Boston), p. 765–775, which book is incorporated herein by reference in its entirety.

The BPD can be incorporated into various polymers, either chemically or mechanically, by those methods disclosed in the references herein before cited and also U.S. Pat. Nos. 4,665,178; 3,882,122; 5,099,027; 4,508,882; and 3,862,087; all of which are incorporated herein by reference in their entirety.

The BPD can be incorporated into various materials, including polymers, as pigments therefor by processes described in U.S. Pat. Nos. 3,97,386; 4,053,463; 4,053,464; 4,334,932; 4,082,741; 4,070,353; 4,065,448; 4,062,838; 4,024,124; 4,006,162; and 4,367,173; all of which patents are incorporated herein by reference in their entirety.

The following specific examples are supplied for the purpose of better illustrating the invention. These examples are not intended, however, to limit or restrict the scope of the invention in any way and should not be construed as providing conditions, parameters, or values which must be utilized exclusively in order to practice the present invention.

EXAMPLE 1

Preparation of 2,5,-Bis(4-hydroxyphenyl)pyrazine (Formula VIII)

A 500 ml three-neck round-bottom flask is fitted with a magnetic stirrer, nitrogen inlet, heating mantle, thermometer, and an upright water-cooled condenser. The vessel is charged with α-amino-4-hydroxyacetophenone acetate salt (AHAP.AcOH), 10.0 g (containing 6.69 g AHAP free base). Potassium acetate, 11.6 g, is added, followed by 160 g DMSO.

The contents of the vessel are heated to 70° C. and the temperature is maintained at 70° C. with stirring for three hours. The reaction is allowed to cool to 50° C. and the nitrogen is discontinued. Air is bubbled into the reaction overnight (16 hours) at 50° C. A dark red solution is observed and is obtained by filtering hot and the filtrate is diluted with 508.5 g distilled water which creates an exotherm. The aqueous reaction mixture is allowed to cool to ambient temperature (i.e. about 20° C.) and crystallization is allowed to continue for six hours. The dark supernatant liquid is syphoned off and the remaining slurry is gradually and gently suction-filtered on a Buchner filter.

The filtrate is rinsed with 150 g of deionized water. The product is air-dried for four hours, then is dried at house vacuum at 60° C. overnight. The residual yellow solid (4.1 g) is submitted for liquid chromatograph (LC) analysis. Purity by LC is 94.8%. FTIR, $^1H$ and $^{13}C$-NMR are consistent with the assigned structure of 2,5-bis(4-hydroxyphenyl)pyrazine. Mass spectroscopy confirms the expected MW 264. The yield of the pyrazine, based on AHAP, is 66.7%

EXAMPLE 2

Preparation of 2.,5-Bis(4-hydroxyphenyl)pyrazine from 4-Hydroxyacetophenone

A two liter five-neck round-bottom flask is charged with 4-hydroxyacetophenone (4-HAP) (100 g, 0.74 mol) followed by the addition of 286 g water and 31% of aqueous HCl (383.3 g, 3.31 mole). The reaction mixture is stirred and heated to 55° C. Aqueous solution of 42% $NaNO_2$ (286 g, 1.62 mol) is added to the generator at a rate of 2.9 grams per minute (100 minute addition). The temperature is maintained at 55° C. After $NaNO_2$ addition is complete, the reaction is continued for another thirty minutes to remove the remaining NOCl. Analysis of the reaction mixture indicates the presence of 9.89 weight percent HPGO (hydroxyphenyl glyoxal) which corresponds to a HPGO yield of 83.3%. The reaction mixture is then cooled to 40° C. and then hydroxylamine free base (112 g, 0.882 mol) is added over a period of ninety minutes. After the addition is complete, the reaction mixture is cooled to 5° C. Filtration affords a solid (114 g). Analysis indicates that the solid contains 14% $H_2O$, 76% HINAP (4-hydroxyisonitrosoacetophenone), 3% HPGO, 2% 4-HAP and 4% unknown. This corresponds to isolated HINAP to be 72%.

Dry HINAP (13.8 g, 0.082 mol, from the above procedure) is added to a 300 ml autoclave, which is charged with 1.38 g of 50% wet (5% palladium on carbon) and 175 ml of dry EtOH and catalytic amount of HOAc (1 ml). The reactor is sealed then degassed three times with nitrogen and three times with hydrogen. The reactor is then pressurized to 50 psi with hydrogen and stirred at 1200 rpm. The reaction consumes two equivalents of hydrogen. The rate of hydrogen consumption is very slow. The reaction is allowed to react a ambient temperature for 19 hours. The reaction heats itself from 22° C. to 27.6° C. The reaction mixture at the end of the reaction is a slurry. Air is bubbled through the reaction mixture to aromatize the dihydropyrazine to pyrazine. The insoluble mixture of the pyrazine monomer and the palladium catalyst are treated with 10% NaOH to pH=8. The reaction mixture is stirred until all the pyrazine is dissolved and only then is the catalyst filtered. The reaction mixture is treated with acid to pH=6 and the mixture is concentrated under reduced pressure. Analysis indicates the presence of the pyrazine [2,5-bis(4-hydroxyphenyl)pyrazine] as the major product in 60% yield (75% selectivity).

This example shows the preparation of a substituted pyrazine via the "in-situ" formation of AHAP without the necessity of actually having to form the AHAP, separating it and then reacting it in the presence of a dipolar aprotic solvent and a base material as shown in step (4), Scheme 1 above.

EXAMPLE 3

Preparation of 2,5-Bis(4-hydroxy-3-nitrophenyl)pyrazine (Formula III, x=1 and y=1)

To a three-neck two-liter round-bottom flask equipped with a magnetic stirrer there is charged 883 grams (9.88 moles) $HNO_3$ (70.5%). The contents are continuously stirred and maintained at 5° C. with the provision of an ice bath. Fifty-three grams of 2,5-bis(4-hydroxyphenyl) pyrazine (Example 2 ) are added to said flask, in ten-gram portions, in order to maintain a 10° C. temperature level of the flask contents. Upon the addition of pyrazine, the solution turns red. After the pyrazine addition is complete, the ice bath is removed and the flask contents are allowed to warm to room temperature (approximately 20° C.). Stirring is continued at room temperature for an additional hour. The product is precipitated by slowly pouring it into four liters of deionized water. The resultant mass is stirred for thirty minutes and then is filtered. The product crystals are washed with four liters of deionized water. The crystals are air-dried with suction on a fritted funnel and placed in an oven at 100° C. under vacuum overnight. NMR identifies the material to be the compound of Formula IX above.

EXAMPLE 4

Preparation of 2,5-Bis(4-hydroxy,3,5-nitrophenyl)pyrazine (Formula III, x=2 and y=2)

To an eight-ounce screw cap bottle fitted with a magnetic stirrer there is charged 72 grams (0.81 moles) $HNO_3$. Four grams of pyrazine are added in portions in order to maintain the resultant mixture at less than 10° C. The mixture becomes red upon addition of 2,5-bis(4-hydroxyphenyl)pyrazine (Example 2). After the pyrazine addition is complete, the ice bath is removed and the overall reaction mass is allowed to warm to room temperature (approximately 20° C.). The contents are then stirred at 20° C. for 16 hours. The contents are then cooled to 5° C. by the use of an ice bath and then 36 grams concentrated sulfuric acid is added, dropwise, to the reaction mass while continuously stirring. The dropwise addition facilitates maintaining the contents' temperature at less than 12° C. The resultant mixture becomes orange upon addition of sulfuric acid. The reaction mixture is then stirred for an additional 16 hours. The product is precipitated by slowly pouring it into 380 grams of ice water. The overall mixture is stirred for 20 minutes and then vacuum filtered. The resultant crystals are then rinsed with an additional 380 grams of deionized water. The crystals are air-dried with suction on a fritted funnel and dried in an oven at 100° C. under vacuum overnight. NMR identifies the material to be the compound of Formula III above where x=2 and y=2.

EXAMPLE 5

Sulfonation of 2,5-Bis(4-hydroxyphenyl)pyrazine

To a three-neck 100 ml round-bottom flask fitted with an ice bath and mechanical stirrer there is charged 60 grams of fuming sulfuric acid (30% oleum) while stirring. Ten grams of 2,5-bis(4-hydroxyphenyl)pyrazine is added in portions and the temperature is maintained at 50° C. Stirring is then conducted for four hours at 50° C. The product is precipitated by pouring the contents into 30 grams of deionized water. The overall mixture is filtered via vacuum and air-dried. NMR identifies the material to be 2,5-bis(4-hydroxy-3-sulfonic acid phenyl)pyrazine.

EXAMPLE 6

Hydrogenation of 2,5-Bis(4-hydroxy-3-nitro phenyl)pyrazine (Formula IX)

To a 100 cc autoclave equipped with a hydrogen inlet and a heating jacket there is charged 5.0 grams (0.01 moles) of dinitro "pyrazine", 0.2 grams of Pd/C catalyst and 47.0 grams of DMF. The autoclave is heated to the temperatures indicated below for the period of time set forth below and hydrogen gas supplied at the pressures indicated below:

| Temp °C. | Time (Hours) | $H_2$ Pressure (psi) |
| --- | --- | --- |
| 50 | 0.5 | 1 |
| 75 | 1.5 | 1 |
| 100 | 2.5 | 100 |
| 100 | 1.0 | 200 |
| 100. | 0.5 | 300 |
| 100 | 1.0 | 425 |

At the end of this 7.0 hour run, the autoclave is cooled by removing the heating fluid and then the contents removed and filtered over celite. The autoclave is washed with DMF and combined with the overall reaction mass which is then filtered. The filtrate is precipitated via pouring in water. The overall mixture is filtered via vacuum and the solids are air-dried on a fritted funnel. NMR identifies the material to be a compound having the Formula XI above.

EXAMPLE 7

Preparation of 2,4,6-tri[2,5-Bis(p-hydroxyphenyl pyrazine]-1,3,5-Triazine

To a two-liter, three-neck, round-bottom flask equipped with a magnetic stirrer there is charged 18.3 grams (0.1 mole) trichlorocyanurate, 79.2 grams (0.3 moles) 2,5-bis(4-hydroxyphenyl) pyrazine, 12.0 grams (0.3 moles) NaOH, and 60 milliliters of NMP. With continuous stirring, the resultant reaction mass is heated to 100° C. and maintained at this temperature for 7.5 hours. At the end of this time, heating is discontinued and the reaction mass is allowed to cool to room temperature (approximately 20° C.). Stirring is continued at room temperature for one additional hour. The product is precipitated by slowly pouring it into four liters of deionized water. The resultant mass is stirred for 30 minutes and then filtered. The product crystals are washed with four liters of deionized water. The crystals are air-dried with suction on a fritted funnel and placed in an oven at 100° C. under vacuum overnight. NMR identifies the material to be the compound of Formula II, i.e. the above-described triazene.

EXAMPLE 8

Preparation of 2.,5-Bis[4'-hydroxy-3'-(2-nitrophenyl azo)phenyl]pyrazine

To a two-liter, thee-neck, round bottom flask equipped with a mechanical stirrer, digital thermometer, heating mantle, and nitrogen inlet there is charged (a) 260 ml tap water; (b) 16 ml of a 50% by weight solution of sodium hydroxide (0.2 moles); (c) 15.0 grams (0.1416 moles) of sodium carbonate (soda ash); and (d) 83.4 grams (0.20 moles) of 2,5-bis(4 -hydroxyphenyl)pyrazine The resultant mass is stirred overnight. Two hundred grams of ice is added to the flask and the overall contents are stirred for 30 minutes (the internal temperature is 0° C.). The diazo compound (166.8 grams) and the orthonitroaniline (converted to a diazonium solution) are placed in an addition funnel and are added dropwise to the contents of the flask over period of two hours, The temperature rises to 15° C. toward the end of the addition and the resultant mass contents are stirred overnight without temperature control. The azo dye product precipitates and is removed from the solution by suction filtration using a course-sintered glass funnel. The wetcake is approximately 30% by weight solids and is dried in a vacuum oven overnight at 100° C. NMR analyses show the product to have the formula:

In addition to the chemical name set forth in the title of Example 8, the product also has the name 4,4'-(2,5-Pyrazinediyl)Bis[2-[(2-Nitrophenyl)Azo]-Phenol].

EXAMPLE 9

Preparation of a Polysulfone Copolymer Using 2,5-Bis(4-hydroxy-3-aminophenyl) pyrazine To a three-neck, one-liter flask fitted with a thermowell, mechanical stirrer, and distillation head there is added bisphenol-A (22.8 g, 0.10 mol), 4-fluorophenylsulfone (29 g, 0.10 mol), 2,5-bis(4-hydroxy-3-aminophenyl)pyrazine (0.267 g, 0.001 mol) and potassium carbonate (27.88 g, 0.20 mol). Once all the reactants are added, 150 g of N-methylpyrrolidinone and 50 g of toluene are added, and the mixture is stirred at room temperature until most of the reactants dissolve. The pale yellow solution is stirred while the temperature is increased from 25° C. to 165° C. over a two-hour ramp. Removal of the water is accomplished by azeotroping with toluene. The temperature is held at 165° C. for sixteen hours, then ramped to 175° C. in five minutes and is held there for two hours. A dark brown solution forms and is allowed to cool to room temperature. The solution is decanted from the residual salts and precipitates into isopropanol/acidified water, 75/25. The resulting solid is filtered, re-dissolved into THF, and precipitated again into isopropanol. The resulting white polymer is filtered and dried in a vacuum oven at 100° C., yield 48 g. The intrinsic viscosity, measured in 1,1,2,2-tetrachloroethane at 30° C., is 0.35. This polymer shows an increase in thermal properties and chemical resistance.

EXAMPLE 10

Preparation of a Polyarylate Copolymer Using 2,5-Bis(4-hydroxy-3-aminophenyl)pyrazine A heterogeneous solution of 2,5-bis(4-hydroxy-3-aminophenyl)pyrazine (2.99 g, 8.7 mmol), bisphenol-A diacetate (2.68 g, 8.6 mmol), terephthalic acid (0.71 g, 4.3 mmol) and isophthalic acid (2.14, 12.9 mmol) is heated to 240° C. in 50 g Dowtherm A (a 50:50 weight ratio of bisphenol A diacetate to pyrazine). The reactants dissolve at 240° C. to form a clear yellow solution. A white precipitate forms with prolonged heating. Heating is continued for an additional four hours at 260° C. A white precipitate is recovered by filtration and washed several times with acetone to remove any residual Dowtherm A, yield 75%. The white polymer melts at 266° C., as measured by DSC. This polymer displays an increase in crystalline structure and strength and exhibits liquid crystal properties.

EXAMPLE 11

The procedure set forth in Example 10 is repeated, however, the ratio of bisphenol-A to pyrazine is changed to 80:20, respectively. A melting point is detected at 266° C., along with a broad exotherm centered at 400° C. Properties

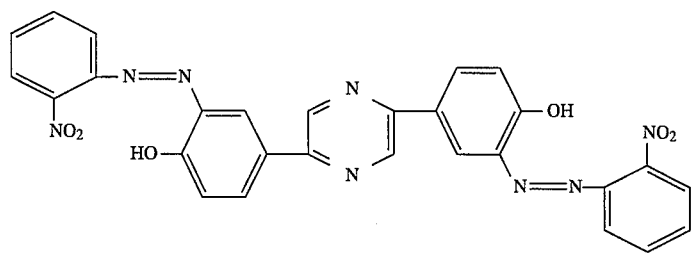

of this polymer are similar to those of the polymer in Example 10.

EXAMPLE 12 (COMPARATIVE)

The procedure set forth in Example 11 above is used to make a bisphenol-A based polyarylate without the incorporation of the pyrazine therein. Thermal analysis of this polymer shows only a glass transition temperature at 195° C., no melting point is observed. This polymer is inferior than that polymer of Example 11 which incorporates the pyrazine.

EXAMPLES 13–27

Preparation of Polymer Compositions

Various polymer compositions comprising the particular polymer having incorporated therein the specific substituted pyrazine are prepared using known methods in the polymer composition art (such as U.S. Pat. No. 4,716,234). The specific polymers are set forth in Table 1. The pyrazine formula is that compound which is disclosed herein above in structural formula. The polymers listed in Table 1 are those polymers which are found to be suitable to have the pyrazines (listed) used therein. Each of these pyrazines are found to be suitable in the (listed) polymers and enhance the physical and chemical properties thereof.

TABLE 1

| Example No. | Pyrazine Formula | Polymer | Comments* 1 | 2 | 3 |
|---|---|---|---|---|---|
| 13 | II | Polyester | + | + | + |
| 14 | III (x & y = 2) | Polyester | + | + | + |
| 15 | IV | Epoxide | + | + | + |
| 16 | V | Polyetherketone | + | + | + |
| 17 | VI ($R_{14-17}$ = H) | Polycarbonate | + | + | + |
| 18 | VII ($R_{18-19}$ = H) | Epoxide | + | + | + |
| 19 | IX | Polyimide | + | + | + |
| 20 | X | Polyamide | + | + | + |
| 21 | IX | Polyamide-imide | + | + | + |
| 22 | XI | Polyarylate | + | + | + |
| 23 | II | Polyetherketone | + | + | + |
| 24 | XIII | Polycarbonate | + | + | + |
| 25 | XIV | Polyamide | + | + | + |
| 26 | XVII | Epoxide | + | + | + |
| 27 | XVI | Epoxide | + | + | + |

*1. Increase in thermal properties (over base polymer)
2. Increase in tensile strength (over base polymer)
3. Increase in modulus (over base polymer)

The novel substituted biphenyl pyrazines of this invention are highly colored materials and suitable for use as dyes and pigments.

EXAMPLES 28–32

The novel compounds are useful as dyes, particularly for hydrophobic fibers, e.g., polyester fiber and blends of polyester with cotton, polyacrylonitrile fiber, etc. The dyeing procedure frequently employed is the thermosol dry heat process. For example, a dye paste is prepared by sand milling a mixture of 7.6% (2,5-bis(4-hydroxy-3-nitrophenyl) pyrazine (from example 3 above) and 15.2% lignin sulfonic acid dispersing agent in water. A sample of a 65/35 polyester/cotton blend fabric is padded at room temperature to 50% pickup, based on the dry fabric weight, in a dye bath prepared by addition of the dye paste to water at the rate of 5.9 g paste to 1 liter of water. The padded material is passed through an infrared pre-drier, dried further in a dry box at 180° F., and then heated at 415° F. for 90 seconds. The fabric is then padded at 100° F. in a bath containing 40 g per liter of sodium hydrosulfite and 50 g/liter of sodium hydroxide. The material is steamed for 30 seconds at 212°–220° F., rinsed in water at 80° F. for two minutes, and oxidized for ten minutes in a bath at 120° F. containing 2.5 g/liter of sodium perborate and 1 g/liter of acetic acid. The fabric is then rinsed in water at 80° F. and soaped for five minutes at 200° F. in a bath containing two g/liter of a sodium ether-alcohol sulfate and 1 g/liter of sodium carbonate. Finally, the cloth is rinsed in water at 80° F. and air-dried at 180° F. The cloth is dyed a yellow. The dye exhibits excellent sublimation fastness. In a similar manner, the substituted biphenyl pyrazines (from examples 4, 5, 6, and 7 above) are successfully used to dye the polyester in a fabric of 65/35 polyester/cotton blend.

EXAMPLE 33

To a solution of 0.02 g of the sulfonic acid-paste product of Example 28 in 2 ml of water is added 0.41 g of multifabric swatch. The pH is about 2–3. The fabric is heated at 51° C. for 15 minutes, removed, rinsed three times with water, and dried at 100° C. in a vacuum oven. Nylon is dyed bright yellow; flanking sections of polyester and polyacrylonitrile remain white; silk is dyed medium yellow-brown; wool, yellow; acetate, Acrilan 1656 and Arnel pale yellow; cotton, Verel T5, and viscose very pale yellow.

When the pH is adjusted to above pH 11 with 0.2 ml 1N NaOH and the dyeing process repeated, no dyeing of the cloth occurs.

EXAMPLE 34

A small sample of the product of Example 3 is ground between glass plates using toluene as a lubricant. Then Datakoat (a toluene-soluble, plasticized acrylic resin in a spray can by Datak Corp., Pasaic, N.J.) is sprayed on the finely divided mixture and thoroughly mixed by rubbing between glass plates and scraping with a razor blade. The yellow mixture is applied to paper and dried to give a bright yellow smudge-proof finish.

In another facet of the present invention, it has been found that the novel BPD are useful as pH-sensitive pigments. In these cases, the BPD are one color in their original form but when exposed to a basic material (such as $NA_2CO_3$ and/or $NaHCO_3$) turn a different color and then, upon further exposure to an acidic material (such as HCL), they return to their original color. Thus, where one incorporates such BPD in a crating composition along with a basic material and the color turns different and this crating composition is applied to a pipe carrying acid, if such pipe were to leak acid, the crating composition would turn a different color (i.e. back to the original BPD color) and be indicative (or an indicator) that the pipe was leaking acid. The utility of this facet of the present invention is quite unique.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound having the formula:

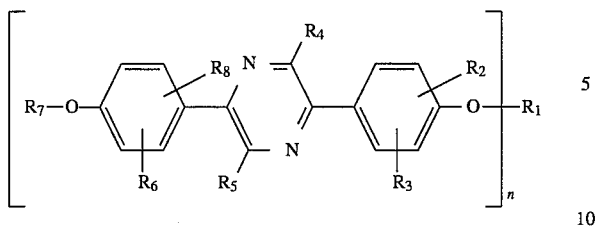

wherein n is 1 or 3, with the proviso that
A) where n is 1,
R$_1$ and R$_7$ are each independently selected from the group consisting of H and —CH$_2$—C$_6$H$_5$
R$_2$, R$_3$, R$_6$, and R$_8$ are each independently selected from the group consisting of H, halogen, NO$_2$, NH$_2$, N$_2^\oplus$, SO$_3$H, SO$_3$M (where M is an alkali metal), C$_6$H$_5$, —OR' where R' is C$_{1-8}$,

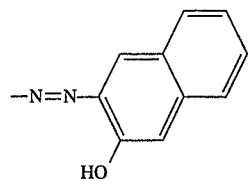

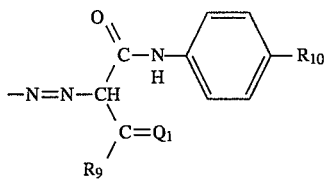

where R$_9$ and R$_{10}$ are each H, C$_{1-6}$, COOCH$_3$, and COOC$_2$H$_5$, and Q$_1$ is NH or O;

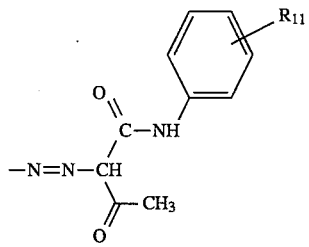

where R$_{11}$ is C$_1$–C$_6$;

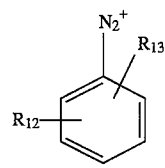

where R$_{12}$ and R$_{13}$ are each independently selected from the group consisting of H, NO$_2$, Cl, OCH$_3$, CH$_3$, COOH, COOCH$_3$, NH$_2$,

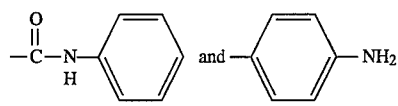

with the proviso that at least one of R$_2$, R$_3$, R$_6$, and R$_8$ must be other than H;
(B) where n is 3,
R$_1$ is

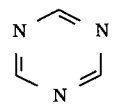

and R$_2$, R$_3$, R$_6$, R$_7$, and R$_8$ are the same as (A) above;
C) where n is 1 or 3, R$_4$ and R$_5$ are each independently selected from the group consisting of H, NO$_2$, NH$_2$, and

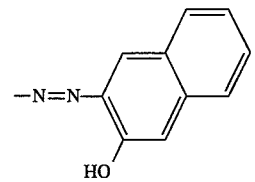

D) where n is 1 and R$_2$, R$_3$, R$_4$, R$_5$, R$_6$, and R$_8$ are H, R$_1$, R$_7$ are not H.
2. The compound of claim 1 wherein n is 1.
3. The compound of claim 1 wherein n is 3.
4. A compound of the formula:

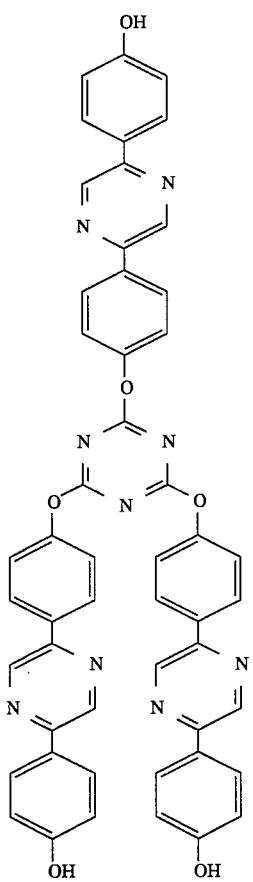
5. A compound having the formula:
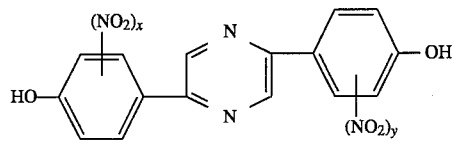
where x and y are each independent and are either 0, 1, or 2, with the proviso that at least x or y must be 1 or 2 when the other is 0.
6. A compound having the formula:
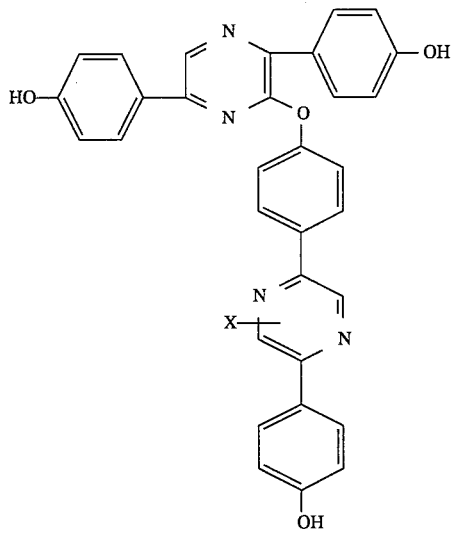
wherein x is selected from the group consisting of chlorine, bromine, and fluorine.
7. A compound having the formula:
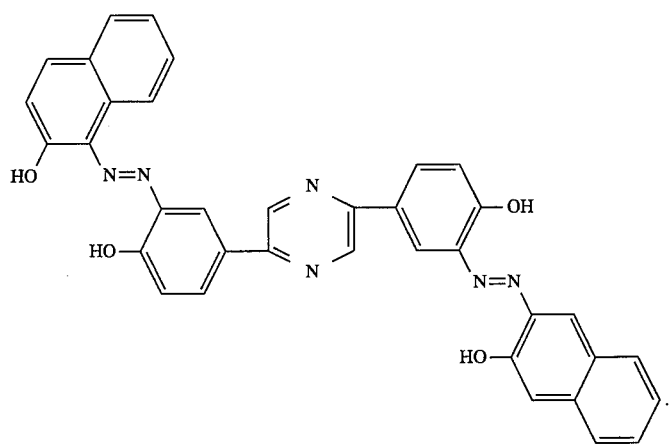

8. A compound having the formula:

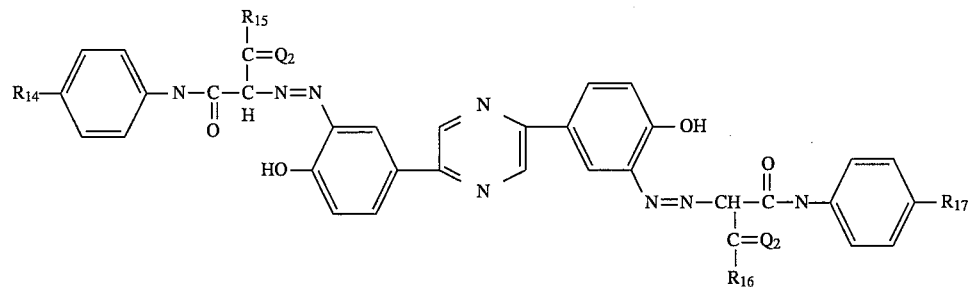

wherein $R_{14}$, $R_{15}$, $R_{16}$, and $R_{17}$ are each independently selected from the group consisting of H, alkyl $C_1$–$C_6$, $COOCH_3$, and $COOC_2H_5$, and $Q_2$ is NH or O.

9. A compound having the formula:

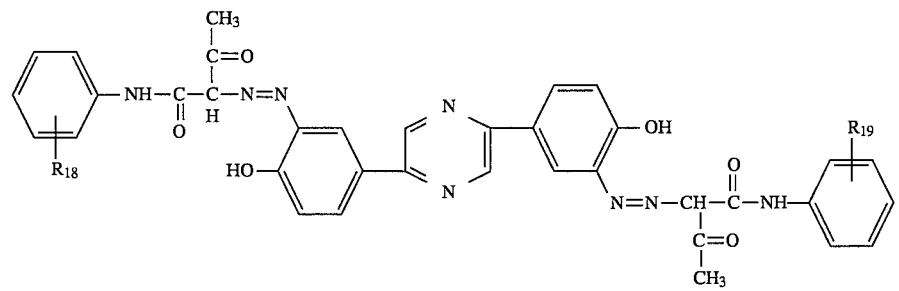

wherein $R_{18}$ and $R_{19}$ are each independently selected from the group consisting of H, alkyl $C_1$–$C_6$, $COOCH_3$, and $COOC_2H_5$.

10. The compound of claim 5 wherein x and y are both 1.

11. The compound of claim 1 wherein n is 1; $R_1$ and $R_7$ are each H; $R_2$ and $R_8$ are each $SO_3H$; $R_3$ and $R_6$ are each H; and $R_4$ and $R_5$ are each H.

12. The compound of claim 1 wherein n is 1; $R_1$ and $R_7$ are each H; $R_2$ and $R_8$ are each $NH_2$; $R_3$ and $R_6$ are each H; and $R_4$ and $R_5$ are each H.

13. A compound having the formula:

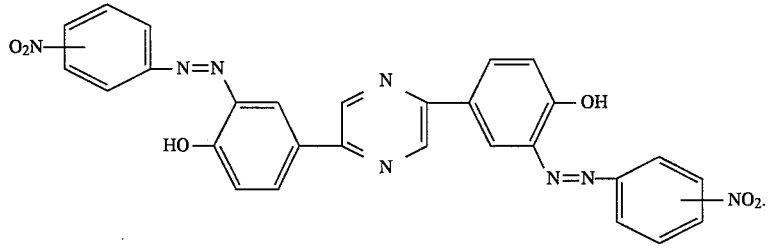

14. The compound of claim 5 wherein x and y are both 2.

* * * * *